United States Patent [19]

Tirino

[11] 4,238,189
[45] Dec. 9, 1980

[54] METHOD AND APPARATUS FOR MAKING IN A SINGLE OPERATION A BASE AND DENTAL MODEL INCLUDING A TOOTH DIE WITH AN INTEGRAL BAYONET TYPE MOUNTING PIN

[76] Inventor: Angelo C. Tirino, c/o Tirino Dental Studios, 299 Smithtown Blvd., Nesconset, N.Y. 11767

[21] Appl. No.: 61,679

[22] Filed: Jul. 30, 1979

[51] Int. Cl.³ .................. A61C 13/00; B29C 5/00
[52] U.S. Cl. .................... 433/74; 264/16; 264/225
[58] Field of Search .................... 264/16–19, 264/225; 433/74, 213; 85/10 R, 11

[56] References Cited

U.S. PATENT DOCUMENTS

| 401,343 | 4/1889 | Gildemeyer | 85/49 |
|---|---|---|---|
| 451,213 | 4/1891 | Shepley | 85/28 |
| 1,110,091 | 9/1914 | White | 85/49 |
| 1,639,530 | 8/1937 | Payson | 85/49 |
| 1,675,178 | 6/1928 | Koch | 85/10 R |
| 1,755,553 | 4/1930 | Monteith | 85/10 R |
| 1,780,117 | 10/1930 | Craigo | 433/74 |
| 2,067,359 | 1/1937 | Tumminello | 85/49 |
| 2,314,481 | 3/1943 | Crooks | 52/717 |
| 2,323,362 | 7/1943 | Weiss | 174/159 |
| 2,533,062 | 12/1950 | Spink | 85/49 |
| 2,851,728 | 9/1958 | Spalten et al. | 433/74 |
| 3,153,283 | 10/1964 | Weissman | 403/292 |
| 3,226,827 | 1/1966 | Spalten | 433/74 |
| 3,436,829 | 4/1969 | Jermyn | 433/74 |
| 3,470,614 | 10/1969 | Kelly | |
| 3,495,333 | 2/1970 | Kuhn | 340/347 R |
| 3,704,519 | 12/1972 | Lystager | 30/34.1 |
| 3,798,772 | 3/1974 | Eberhard | 433/74 |
| 3,937,773 | 2/1976 | Huffman | 433/74 |
| 4,021,916 | 5/1977 | Spalten | 433/74 |
| 4,172,867 | 10/1979 | Devault | 264/16 |

FOREIGN PATENT DOCUMENTS

2456763 7/1975 Fed. Rep. of Germany .......... 85/10 R

Primary Examiner—W. E. Hoag
Attorney, Agent, or Firm—Kevin Redmond

[57] ABSTRACT

A method for producing in a single casting operation a dental model including a unitary tooth die which incorporates an integral mounting pin. The pin and die form a part of, and are removable from the dental model. Prior to casting the die, a bayonet shaped mounting pin is held in position by a permanent divider which, in turn, is supported in a negative impression of a denture. The die and base are then cast simultaneously, eliminating the need for the more commonly used double casting procedure.

6 Claims, 10 Drawing Figures

METHOD AND APPARATUS FOR MAKING IN A SINGLE OPERATION A BASE AND DENTAL MODEL INCLUDING A TOOTH DIE WITH AN INTEGRAL BAYONET TYPE MOUNTING PIN

BACKGROUND

1. Field

The present invention pertains to prosthetic dentistry and more particularly, to a simple and convenient single mounting pin as well as a means for casting a base and dental model with a removal die all in a single operation.

2. Prior Art

A typical assembly for prosthetic dentistry is shown in FIG. 1. This assembly comprises a base 101 with an opening 107, a model 102 secured to the base, a die 103 which is removably attached to said base and a mounting pin 105 secured to the die.

As can be seen in FIG. 1, a replica of the tooth to be reproduced, referred to as the die 103, is made so that it may be removed from the base 101. The removable feature facilitates fabrication of the selected tooth from the die. The die is formed at the same time as the replica of the adjoining teeth, assuring a proper fit with respect to these teeth.

Since the replica of the adjoining teeth, referred to as the dental mode 102, are permanently attached to the base, the pin must align the die with the base and simultaneously with the replica of the adjoining teeth. This alignment is usually accomplished by casting the die about the pin and then in a separate operation, casting the base about the remainder of the pin. These two casting operations may take up to 45 minutes each. It would be preferable if both could be accomplished at the same time. The need for the double casting operation is due to the fact that in conventional systems some means is necessary to support the pin while the casting material sets about that portion of the pin which is within the die. This means of temporarily supporting the pin is removed and then the base is cast.

The die is cast using a mold which is a negative impression of a denture, such as that shown in FIG. 2. In this Figure, a pin 105 is held in place in a negative impression 201. This impression is designed to accept, in the area about the pin, a suitable casting material such as gypsum to form the die with a portion of the pin secured within it.

After the casting material in the die has set, the support means for the pin in a conventional system is removed and the base is poured in a separate, second operation.

In some instances a plastic sleeve is used to cover the portion of the pin which is to be embedded in the base so that after relieving and cleaving the die, the pin may be removed from the base without difficulty.

The usual relieving and cleaving procedures carried out after the die, model and base have hardened consist of cutting through the casting material on either side of the die to carry out the relieving operation. The cleaving operation is carried out by cutting the material across the bottom of the die. This allows the die to be separated from the model and base. The lines along which these operations are carried out is shown in FIG. 3, wherein a dental model 304 is shown to include a die 305 with an integral alignment pin 306. The die is relieved along lines 301 and 302 and cleaved along line 303.

A number of different shaped pins are currently in use. The most commonly used pins are shown in FIGS. 4 through 8. FIG. 4A shows the side view of a first pin 401, while FIG. 4B shows a cross sectional view of this pin. The flat leading edge 402 is intended to prevent this pin from rotating in the base, but, unfortunately, the trailing edge 403 is round and the result is the pin tends to break the gypsum after a few insertions and rotate in the opening in the base.

FIG. 5 shows a second type of pin and its associated sleeve. FIG. 5A shows a side view of this pin, while FIG. 5B shows a cross sectional view. FIG. 5C shows a side view of a sleeve adapted to accept this pin. The pin is inserted in the sleeve and the sleeve is cast into the base. In this way, the casting material in the base is protected by the sleeve from being broken by the pin. The pin includes a flat area 501 to prevent rotation; however, the complete device including the flat area 501 is usually made so wide that it is not suitable for the smaller anterior, or front teeth.

FIG. 6 illustrates a third type of pin in which FIG. 6A is a side view of the pin, FIG. 6B is a cross sectional view of the pin and FIG. 6C shows a breakaway portion of the associated sleeve. This type of pin is completely round and therefore requires a minimum of two pins to prevent rotation of the die. In addition, carbide drills are required to produce the openings in the base to accept the sleeves. In addition, a machine is required to drill the dental model.

FIG. 7 illustrates a fourth type of pin in which FIG. 7A is a side view and FIG. 7B is a bottom view. This pin requires the stocking of three different sizes to accommodate all the various sizes of teeth.

FIG. 8 shows a mold for a fifth type of pin in which the mold 801 holds two straight pins, 802 and 803, used to secure the mold to the negative impression. The alignment pin itself is formed from the casting material, such as gypsm. It is, therefore, weak in comparison to the other pins which are metal. Unfortunately, this type of pin tends to break off from the die.

With the exception of the last mentioned molded pin, all the pins thus far described require two casting operation, which is both costly and time consuming.

SUMMARY

It is an object of the present invention to generally overcome the disadvantages of the prior art pins including the need for double casting operation required for most of these pins.

The present invention provides a nonrotating, relatively unbreakable metal pin which accommodates all tooth sizes and which eliminates the need for the cleaving operation and the second casting operation as well as eliminating the need for a sleeve or pin mold. The present invention comprises a bayonet shaped pin with two generally wide, flat sides that cannot rotate in the slit-type opening formed in the base to accept this pin. A divider adapted to accept the pin is placed at the level the die is normally cleaved. The pin is supported in its proper position in the negative impression by the divider and the die and base are poured about the pin and divider in one casting operation. There is no cleaving operation necessary as the die is separated from the base by the divider.

DETAILED DESCRIPTION OF THE INVENTION

Figure 9:
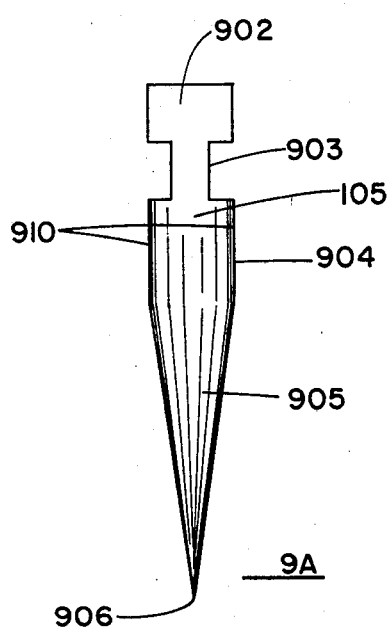
FIG. 9 illustrates a die alignment pin of the present invention.
Figure 9:
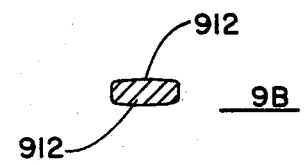

Referring to FIG. 9, a pin 105 fabricated in accordance with the present invention, comprises a cross member 902, a neck 903, an upper blade portion 904 with generally parallel sides 910, a lower tip 906, and a central portion 905 tapering from the tip to the wider upper portion.

FIG. 9B shows a cross sectional view of this pin. The sides 912 can be seen in this view to be generally flat, with only a slight rounding to assist in inserting the pin into the opening in the base. The wide, flat sides overcome the tendency to rotate occurring in some prior art pins, such as those shown in FIGS. 4, 5, 6, and 7. The present invention thus eliminates the need for two pins or pins with a second projection designed to overcome rotation of the die. The wide, relatively flat bearing surface 912 of the present invention and the avoidance of rotation of this device overcome the need for sleeves to protect the base from damage thereby lowering cost and complication.

The parallel edge 910 of the upper portion aligns the pin in the vertical direction. The relatively long length of these sides also permits an up or down adjustment in the base opening while maintaining the proper alignment of the die with respect to the adjacent teeth in the dental model. Completely tapered devices, such as that shown in FIG. 7, fail to offer this advantage because of the possibility of a shift in the die when only the thin portion of the pin is in the opening.

Figure 10:
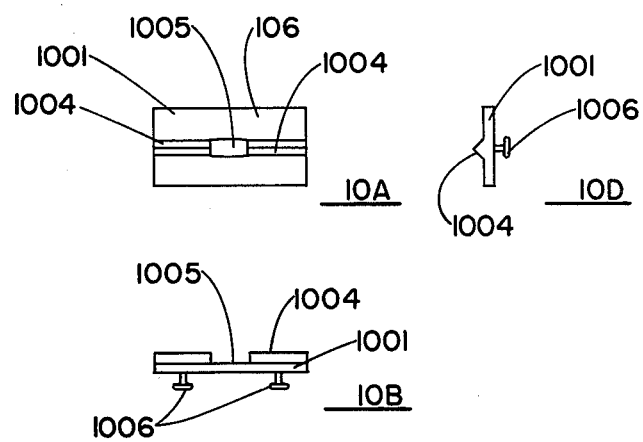
FIG. 10 illustrates a divider used in conjunction with the pin of FIG. 9.
Figure 10:
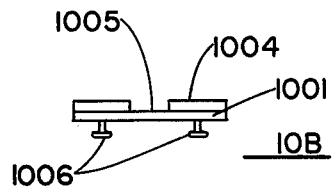
Figure 10:
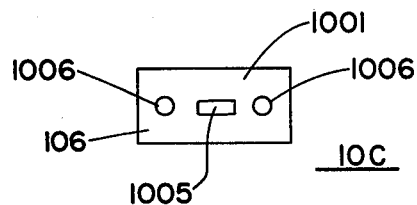
Figure 10:
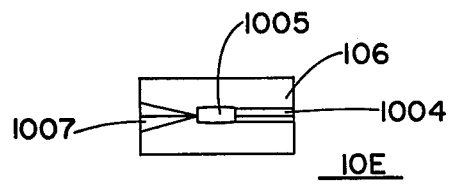

FIG. 10 illustrates a divider used in conjunction with the pin of FIG. 9. FIG. 10A is a top view which shows the divider 106 comprising a flat sheet area 1001, a central opening 1005 and a keyway 1004. The cross section of the opening 1005 corresponds to the cross section of the upper region 904 of the pin 105.

FIG. 10D shows an end view of the divider of FIG. 10A. In this end view, it can be seen that the keyway has a triangular cross section. This is used to assist in properly aligning the die. It can also be seen in this view that the lower side contains anchoring projections 1006 used to secure the divider to the base.

FIG. 10B is a front view of the divider shown in FIG. 10A. This front view shows a plurality of anchoring projections 1006 on the lower side of the divider and a break in the keyway 1004 over the central opening 1005.

FIG. 10C is a bottom view of the divider of FIG. 10A. The location of the anchoring projection 1006 is evident in this view.

The divider is used to separate the die from the base and support the pin in position before casting so that the base, die and complete dental model may be cast simultaneously, eliminating the double casting operation required for most prior art devices.

FIG. 10E is a top view of an alternative configuration of the divider. In this view, it can be seen that the keyway has a widened portion 1007 on one side of the central opening 1005 to provide a means of back-to-front orientation of the die in the dental model.

To facilitate fabrication of the dividers, they are formed on a continuous sheet with perforations at the points where they will be separated for use. Several closely spaced lines of perforations may be used to facilitate providing a particular width quickly and easily during the model preparation.

Figure 2:
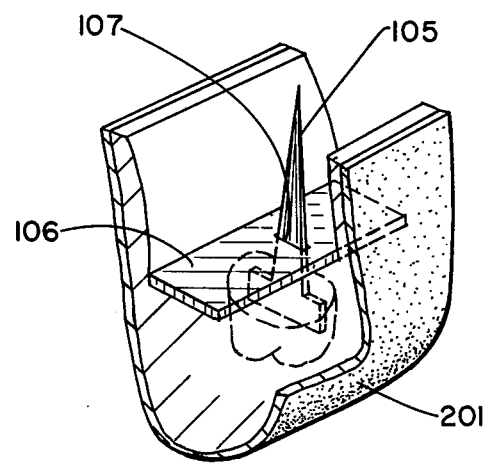
FIG. 2 is a pictorial view of a negative dental impression.

The method of using the divider is shown in FIG. 2. The divider is placed in the negative dental impression 201, at a level where the die is to be separated from the base. The pin 105 is held in place in the central opening of the divider. The divider is the support for the pin during the casting operation, but unlike prior art supports, it does not have to be removed before casting the base. It remains while the die is cast below it and the base is cast above it.

Figure 3:
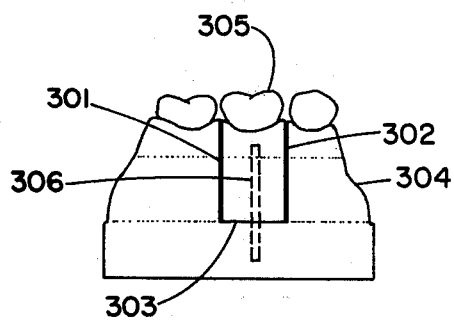
FIG. 3 is a dental model illustrating the lines of relief and cleavage about a removable die.
Figure 4:
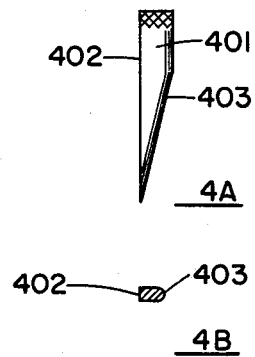
FIG. 4 illustrates a first type of die alignment pin.
Figure 5:
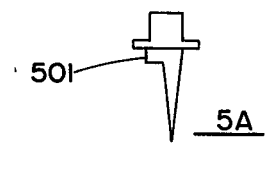
FIG. 5 illustrates a second type of die alignment pin.
Figure 5:
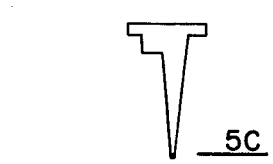
Figure 6:
FIG. 6 illustrates a third type of die alignment pin.
Figure 6:
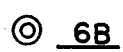
Figure 6:
Figure 7:
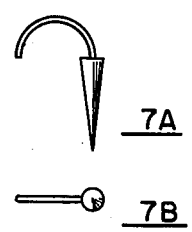
FIG. 7 illustrates a fourth type of die alignment pin.
Figure 8:
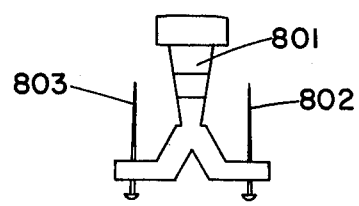
FIG. 8 illustrates a die alignment pin mold.

After the cast has hardened, the die is relieved as shown in FIG. 3. The cleaving operation is eliminated because the divider is located at the line 303, where cleaving would normally take place. The divider is typically made of plastic which does not adhere well to the casting material except where protrusions are extended into the cast, such as anchoring protrusions 1006.

Figure 1:
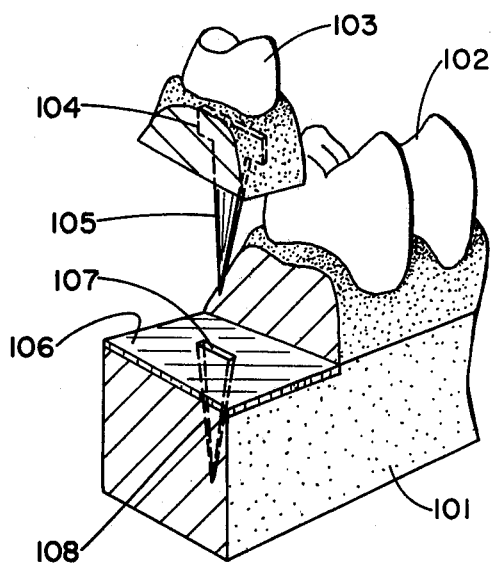
FIG. 1 is a pictorial view of a dental model, a base, and a removable die.

The position of the divider is more clearly shown in FIG. 1. In this Figure, the divider 106 is shown secured to the base 101. This is accomplished by means of the anchoring protrusions 1006, which are cast into the base during the single casting operation. The central opening in the divider is shown positioned over the opening in the base 107. This perfect alignment is produced by virtue of the fact that the pin is held in place in the divider to form the opening 107 during the casting operation. Unlike some prior art devices, no separate drilling operation is necessary to produce this opening, nor is there any possibility of misalignment due to such a drilling operation.

Having described my invention, I claim:

1. A method for forming a unitary tooth die and mounting pin integral with and removable from a dental model and base, comprising the steps of:
   (a) providing a negative dental model including the selected tooth to be reproduced,
   (b) providing a planar divider with a width and breadth sufficient to cover the area in the model over a cavity of a selected tooth to be reproduced, said divider having a central opening generally in the shape of a rectangle,
   (c) providing a generally flat bayonet-shaped pin comprising:
   1. a lower tip having a width less than that of the mouth of said opening to facilitate insertion of said pin in said opening,
   2. an upper portion with a width greater than that of the tip and having generally parallel sides, said upper portion having a cross section generally corresponding to the opening in said divider,
   3. a central portion tapering from the tip to the wider upper portion, and 4. a top portion having a cross member to anchor said pin in said die, (d) inserting said pin up to the center of its upper portion into the divider through said opening in the divider, (e) positioning the divider with the pin inserted in the divider opening over and in alignment with the cavity in the model of the selected tooth to be reproduced, said divider being oriented to place the pin cross member in the cavity of the selected tooth, (f) pouring a dental molding material into the negative impression, about the pin, about the cross member of said pin and the divider to form the die of the tooth to be reproduced and the base in a single pour, (g) allowing the molding material to harden, and (h) relieving the model through the base portion on either side of the pin about the width of the tooth to be reproduced down to the divider to permit removal of the die.

2. An assembly for prosthetic dentistry comprising:

(a) a base, said base being formed with an opening contoured to accept a bayonet-shaped pin, (b) a model secured to said base, (c) a die in said model removably attached to said base, (d) a generally flat, bayonet-shaped pin anchored in said die comprising:

1. a lower tip having a width less than that of the mouth of said opening to facilitate insertion of said pin in said opening, 2. an upper portion with a width greater than that of the tip and having generally parallel sides, 3. a central portion tapering from the tip to the wider upper portion, and 4. a top portion having a cross member to anchor said pin in said die.

3. An assembly as claimed in claim 2, further comprising a generally planar divider positioned between the die and the base prior to forming the die and base to separate the two, when formed, said divider containing a centrally located opening essentially identical in cross section to the opening in said base and positioned to lie over and coincide with said opening in the base.

4. An assembly as claimed in claim 3, wherein said divider is comprised of material having a surface which essentially does not adhere to the material forming said die and base, said divider including a portion with an enlarged end projecting into the base to anchor the divider into the base and said divider including a ridge on the surface contacting the die to serve as a key to align the die with respect to the base.

5. An assembly as claimed in claim 4, wherein said ridge is triangular in cross section to facilitate repositioning the die on said ridge and divider after removal.

6. An assembly as claimed in claim 3, wherein said ridge is triangular in cross section, one end of said ridge being wider than the opposite end to provide for fore and aft alignment of the die.

* * * * *